United States Patent [19]

Arbuckle

[11] Patent Number: 5,651,117

[45] Date of Patent: Jul. 22, 1997

[54] METHOD AND SYSTEM FOR DISSEMINATING OBITUARIES AND ADMINISTERING A DEPOSITORY TO ACHIEVE THIS

[76] Inventor: Gilbert B. Arbuckle, 118 Butler Rd., Quincy, Mass. 02169

[21] Appl. No.: 398,069

[22] Filed: Mar. 3, 1995

[51] Int. Cl.[6] .................................................... G06F 17/60
[52] U.S. Cl. .......................... 395/204; 395/201; 395/203
[58] Field of Search .................................... 395/201, 202, 395/203, 204

[56] References Cited

U.S. PATENT DOCUMENTS

| | | | |
|---|---|---|---|
| 4,491,725 | 1/1985 | Pritchard | 235/375 |
| 4,870,576 | 9/1989 | Tornetta | 364/401 |
| 4,916,611 | 4/1990 | Doyle, Jr. et al. | 395/202 |
| 5,032,989 | 7/1991 | Tornetta | 364/401 |
| 5,127,879 | 7/1992 | Schubert | 462/2 |
| 5,164,897 | 11/1992 | Clark et al. | 364/401 |
| 5,241,466 | 8/1993 | Perry et al. | 364/401 |
| 5,283,731 | 2/1994 | Lalonde et al. | 364/401 |
| 5,502,576 | 3/1996 | Ramsay et al. | 358/444 |

OTHER PUBLICATIONS

Knox et al., "Last wishes: a handbook to guide your survivors", Ulyssees Press, Berkeley, CA 1995 177P, 1995, Dialog file 163, Acc. No. 00065124.

Block, "Do your heirs a favor and spell out your last wishes", Veterinary Economics v36 n11 pp:78–83 Nov. 1995 ISSN: 0042–4862, Dialog File 485, Acc. No. 00545043.

McDougall, "Metro's funeral establishment", Metropolitan Toronto Business Journal (Toronto, ONT, Canada), v83 n4 s1 p18, May 1993, Dialog file 635, Acc. No. 0398253.

Brochure of National Funeral Directors Association, Inc. "What Can We Do to Help?" (undated).

Brochure of National Funeral Directors Association, Inc. "Making Funeral Arrangements" (undated).

Advertisement Brochure of Luce Press Clippings Mesa, AZ. (undated) (Partial).

Advertisement Brochure of Bacon's Clipping Bureau, Chicago, IL (undated) (Partial).

Advertisement Brochure of Burrelle's Press Clipping Service, Livingston, NJ (undated) (Partial).

"Newspapers Race for Outlets in Electronic Marketplace" By William Glaberson, New York Times, Jan. 17, 1994 Sect. D pp. 1,6.

(List continued on next page.)

*Primary Examiner*—Gail D. Hayes
*Assistant Examiner*—Frantzy Poinvil

[57] ABSTRACT

This is a system for disseminating obituaries by a depository that monitors reports of death and selectively transmits some of them to persons who have contracted beforehand with the depository to be notified of certain deaths when report of them is received. The depository creates a database of persons whose deaths are to be reported to customers and a database of customers who are to have certain deaths reported to them. The customer specifies the method of communication and the address to which the death notice is to be sent. The depository monitors all reports of death arising in a domain predetermined in an agreement with the customer and compares data identifying the reported deceased with data identifying the awaited deceased selected by customers. When there is a match the depository transmits a notice of death to the customer at the address and in the manner specified. Customers concerned with publicizing a death are able to report that death to the depository and designate third parties to whom a notice of death or memorial services shall be transmitted. A funeral home using the system departs from its conventional role as a funnel through which material for death notices is channeled to newspapers, opens a new route for the dissemination of obituaries and, in solving the problem attending the direct personal notification of marginal acquaintances, creates a practical option of newspaper bypass.

8 Claims, 6 Drawing Sheets

OTHER PUBLICATIONS

"In San Jose, Knight Ridder Tests a Newspaper Frontier" By William Glaberson, New York Times, Feb. 7, 1994 Sect. D pp. 1,6.

"Times Mirror and Nynex in Venture", By John Markoff, New York Times May 4, 1994 Sect. D, pp. 1,21.

"Is the Times Falling Behind the Times?" By Elizabeth Lesly, Business Week, Dec. 6, 1992, p. 48.

Advertisement for Classifacts, Boston Globe Sep. 4, 1994, p. A19.

Advertisement Brochure of RWS Information, Inc. for Patent Watches. London, England (undated).

Advertisement Leaflet of Rapid Patent for Patent Alert Service (undated).

Advertisement Brochure of Mercury Center, San Jose, CA for Newshound (undated).

Advertisement for Fast Trak New York Times, Jan. 9, 1994 Sect. 11, p. 3.

"The Schwab Revolution," Business Week, Dec. 10, 1994 pp. 88–90.

ND SYSTEM FOR
METHOD AND SYSTEM FOR DISSEMINATING OBITUARIES AND ADMINISTERING A DEPOSITORY TO ACHIEVE THIS

BACKGROUND OF THE INVENTION

1. Field of the Invention

This invention relates to the field of acquiring and transmitting information relating to the deceased and administering a depository to achieve this.

2. Statement of the Problem

Those concerned with responding to the deaths of others have traditionally been obliged to attend to the obituary pages of newspapers. As deaths occur, persons responsible for publicizing these deaths select certain newspapers and provide them with material for death notices, or obituaries. The newspapers then publish the notices in their obituary sections where readers peruse them to learn whether any death has occurred to which they wish to respond. This conventional method of disseminating death notices has many disadvantages.

Monitoring the obituary pages of a newspaper is a time consuming, tedious and sometimes depressing task. Moreover, it is usually fruitless since most such readings announce no death that concerns the reader. Readers know this, yet remain obliged to consult these pages because they realize that they always might announce a death that is important to them. Failure to acknowledge some deaths can have unwanted consequences not only socially but in the world of business and politics. For the elderly, responding to the deaths of others is often a major concern requiring constant attention to the obituary pages of newspapers.

The conventional method of disseminating obituaries also involves uncertainty. If a reader neglects the obituary pages for even a few days they may during that time announce a death that nullifies months of diligent reading. Even if during the period of neglect they announce no death that concerns the reader, the reader who lapses and resumes does not know this and wonders whether a death anticipated has already occurred. If a person wishes to travel when an important death is in the offing the conventional system creates insuperable problems because it is usually impossible for travelers to obtain their regular newspapers.

Further, an important death may be overlooked simply through inadvertence especially by the elderly, those living alone and those intensively engaged in demanding projects. I have suffered social embarrassment through failure to learn of the deaths of others and at one point was reduced to making precarious arrangements with a friend to inform them of a certain death if he learned of it. The conventional system of disseminating death notices provided no way in which one could assure him or herself of timely notice of a given death.

The conventional system also presents needless difficulty to those responsible for disseminating news of a death, especially when the deceased had many friends. After personally notifying a small circle of friends and relatives they must decide which newspapers all others are most likely to read, place notices in them and trust that those who read different newspapers, or who seldom read the obituary pages, will learn of the death some other way. Often the family of the deceased realizes that the one or more newspapers selected are unlikely to convey news of the death to certain interested parties, yet they remain averse to a direct personal notification of some of these parties. This problem has persisted despite the diligent introduction of new services by funeral homes because it stems from a cause deeper than the disinclination to perform demanding social chores during a time of distress.

The source of the problem lies in the psychosocial dynamics beneath the direct personal notification. A direct personal notification implies an expectation that the one thus notified will want to attend the memorial services. If that person will not attend, an unprepared and awkward explanation is apt to be necessary and any lack of tact in giving or receiving it will tend to create the aura of a failed test of friendship. Such an outcome is more than a discomfort for the party notified. It is also a disadvantage for the family because when an acquaintance believes that he or she has offended the family and lost its regard this tends to impair even such relationship as there was. The problem is exacerbated to the degree that the family does not know what the exact nature of the friend's relationship with the deceased really was and hence does not know even how to expect that person to respond. Accordingly, family members frequently accept it as regrettable but inevitable that despite their best use of the conventional system certain friends and acquaintances of the deceased will probably not receive timely news of the death they wish to publicize.

Finally, the dying themselves sometimes worry that distant friends will fail to learn of their death because they can not be sure that their survivors will manage or even undertake to inform all of them.

BACKGROUND—PRIOR ART

A computerized system for administering a depository providing for rapid and efficient communication of information relating to the dying and deceased is disclosed in U.S. Pat. No. 5,241,466 to Perry, Oelsner and Anderson (8/1993). This invention provides for a central depository for storing living wills, powers of attorney, authorization of organ donation and similar information relating to the dying and deceased. The depository receives this information from customers anticipating their own death who want it to be available in the event that a request is made for it. However, the invention does not monitor any source or sources of information for reports of death and does not attempt to discover or communicate that the customer or anyone else has died or is dying. It presumes a knowledge of death or immanent death by one who submits an inquiry to the depository, typically from a hospital, and it transmits information about the deceased or dying only in response to this request from someone already on the scene or already cognizant of the death. Thus it does not envisage and can do nothing toward solving the problem addressed by the present invention.

SUMMARY OF THE INVENTION

The present invention provides for a depository that monitors all reports of death arising in a predetermined domain, screens them and selectively transmits some of them individually to customers who have contracted with the depository to be notified of certain deaths when report of these deaths is received. Customers of the depository identify for it beforehand the person or persons of whose death they wish to be notified, agree upon the source or sources to be monitored and specify the way in which the death notice shall be transmitted. The task of monitoring reports of death thus shifts from individuals who perform it laboriously and imperfectly to a computerized system that accomplishes it with rigor and speed. The depository monitors all reports of death arising in the predetermined domain and compares data identifying the reported deceased with stored data identifying persons designated by customers as persons of whose death the customer is to be notified if a report of the death is received. When a match is found the depository retrieves the information relating to customers concerned with that death and transmits a death notice together with any associated obituary information to the customer or to a party designated by the customer in the manner and at the addresses specified. Customers of the depository thereby gain high assurance that they will receive timely notice of deaths that concern them and at the same time are relieved of the burden of monitoring the obituary pages of newspapers.

Those concerned with disseminating a notice of death or memorial services are able to submit information to the depository and designate third parties to receive it. With the depository acting in his or her stead, the bereaved family member need not even appear as the author of the communication. Those who will not attend the services have an opportunity to compose a written response or even to decide on reflection that it would be better to attend. Any sense of confrontation or test of friendship is blunted and the family member can without awkwardness notify individually persons whose relationship with the deceased is uncertain. When used with supplemental newspaper publication, the method sometimes results in a selection of newspapers different from that made when the conventional system is the only one available. A funeral home acting as the depository departs from its conventional role as a funnel through which material for death notices is channeled to newspapers, opens a new and more certain route for the dissemination of obituaries and, in solving the problem attending direct personal notification, creates a practical option of newspaper bypass.

OBJECTS AND ADVANTAGES

The objects and advantages of the present invention are:

(a) it enables people to obtain notices of deaths that concern them without having to rely upon newspapers or personal acquaintances;

(b) it saves people the time otherwise spent monitoring obituaries in newspapers;

(c) it relieves people of the expense of subscribing to newspapers they would not ordinarily purchase;

(d) it permits people to have a new and incomparably higher assurance that they will receive timely notice of deaths that concern them;

(e) it provides people with a range of choices as to the places at which and the means by which they will be notified of deaths that concerns them, thereby permitting them to travel or to live in seclusion without fear that they will fail to learn of a death to which they wish to respond;

(f) it provides for a speedier notification of deaths than the conventional system;

(g) it gives those responsible for disseminating news of death a more convenient and certain way to complete their task;

(h) it gives the dying a way to be assured that news of their death will reach distant friends.

DESCRIPTION OF THE PREFERRED EMBODIMENT—FIG. 1.

Figure 1:
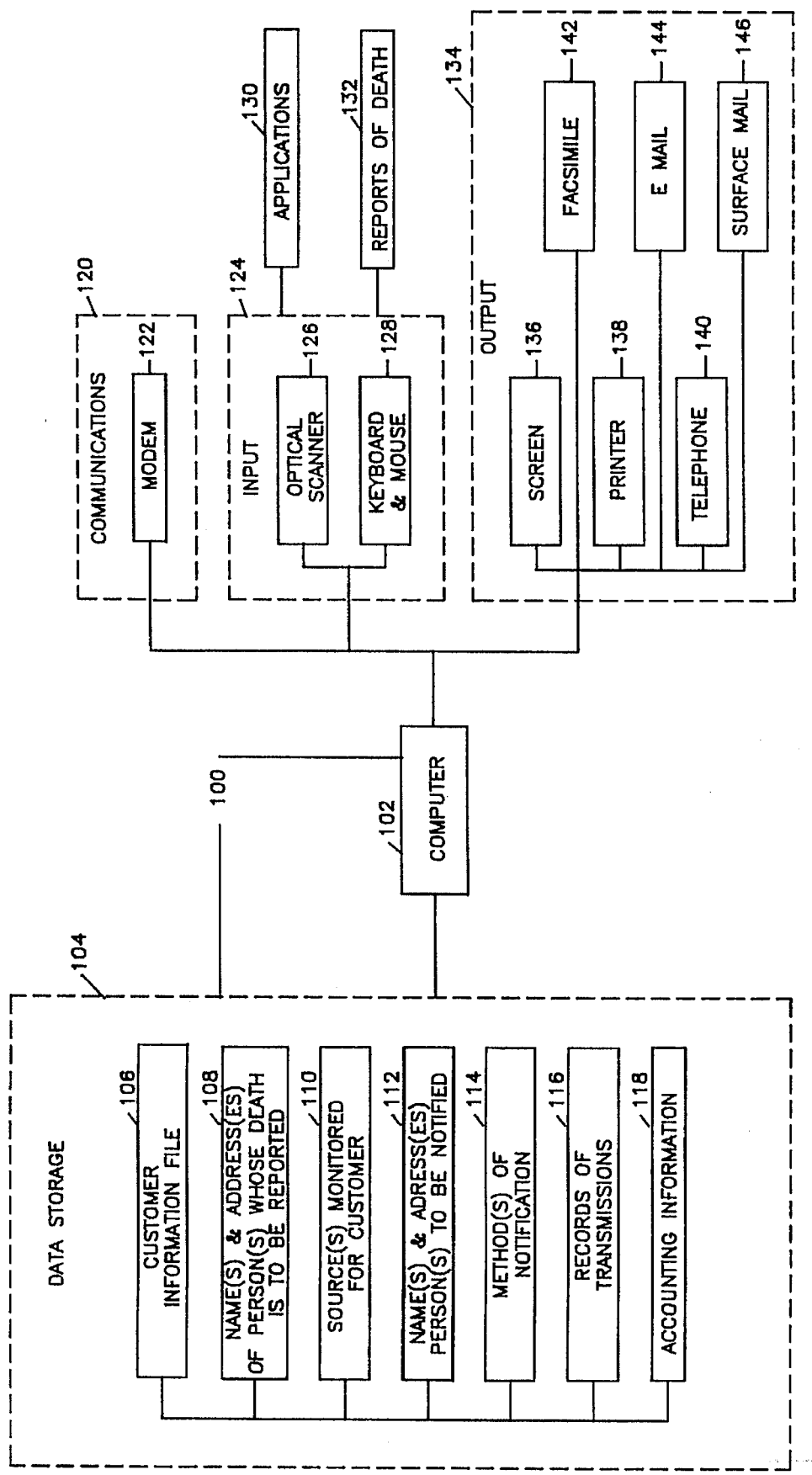
FIG. 1 is an overview of a preferred embodiment of the present invention.

An overview of the preferred embodiment of this invention is presented in FIG. 1. The system provides for a central depository 100, including a computer facility 102, for data storage of information 104 relating to customers who contract with the depository to be notified of the death of a certain person or persons when this occurs. The central depository, 100 can be physically located almost anywhere. The computer 102 receives data input 124 and generates data output 134. Communications facility 120 includes modem device 122 which inputs information to the computer 102 and also transmits information from the system.

For each customer a customer information file 106 is created which specifies the services to be rendered that customer. This file includes the name and address of the person or persons whose death is to be reported when it occurs 108, the source or sources to be monitored for the customer 110, the name and address of the person or persons to be notified 112 and the method or methods by which the death notice is to be transmitted 114. It also includes a record of any transmission or transmissions made for the customer's account 116. Accounting information 118 is present for billing and associated services. The system is also capable of purging itself of information relating to a service after it has been performed and of information relating to inactive customers.

Data input 124 comes from modem 122, optical scanner 126 and keyboard with mouse 128. It includes information obtained from customer applications 130, which may be entered either manually or with the aid of an optical scanner. It further includes reports of death 132 which are obtained by the depository from the source or sources that it monitors. These reports may include additional associated information, such as the time and place of memorial services for the deceased. How these reports of death are obtained will be shown in the following description of the depository operation. These reports and associated information may be entered into the system manually or received by modem 122 in digital form. The system is also capable of receiving new and additional instructions from the customer. These would typically consist in changes of address, changes in the means by which the death notice is to be transmitted and additional names and addresses of persons of whose deaths the customer wishes to be notified.

The depository further includes output 134 to the persons whom it has contracted to notify of certain deaths. Output devices include a screen 136 for visual observation of depository operations, a printer 138 for printing any notices for delivery by surface mail, and devices for telephone 140, facsimile 142, email 144, and surface mail 146 transmissions. Communications facility 120 serves also for output in direct transmission by facsimile and email.

OPERATION

1. Processing the Application—FIG. 2.

Figure 2:
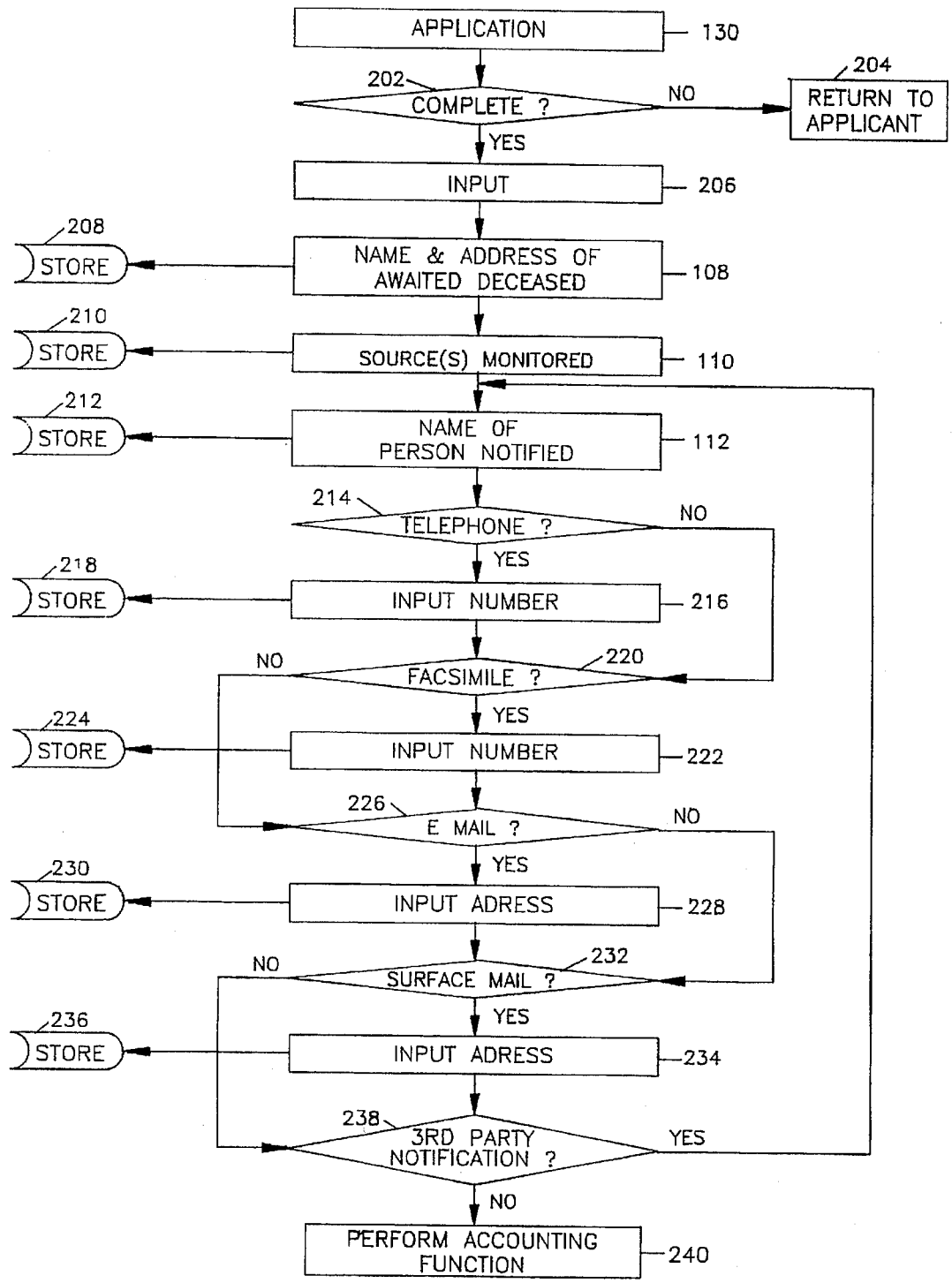
FIG. 2 is a flow diagram of the customer application process of the present invention as used for those concerned with being informed of a certain death.

The depository receives information partly from the customer application form. A flow diagram of the application process is shown in FIG. 2. The application 130 including the customer's name and billing address is taken at the receiving office of the depository and processed either manually or by a computerized system.

At decision block 202 the application is checked for completeness and omissions that would make it impossible to provide the service requested. If, for example, the customer specifies that notice of a certain death is to be transmitted by email, an email address must be given. The application is also checked to see that the service requested falls within the range of those offered by the depository. The depository may reject, for example, requests to transmit a death notice by certain methods to addresses in remote geographical regions. The depository may also define any limits that it sets on its responsibility. It may stipulate, for example, that any death notice to be transmitted by telephone will be deemed transmitted if left on an answering machine responding at the number telephoned. If the information is incomplete or in error the application is returned to the customer at block 204 with a request for additional information. When the application is complete the information is entered into the depository computer as indicated at block 206.

The information on the application form includes the name and address of the awaited deceased 108, who is the person of whose death the customer is to be notified when this occurs. The address of the awaited deceased is obtained because this information, which is included in official death certificates, is sufficient and usually necessary to distinguish between two persons of the same name. The information is stored as shown at block 208. The application also specifies the source or sources 110 to be monitored for reports of death, which is stored as shown at block 210. This source or set of sources that the depository monitors may be the same for all customers. In this case the application acknowledges agreement as to the depository's responsibility with respect to sources monitored. The information on the application also includes the name of the person to be notified of the death 112 which is storm as shown at block 212. This party to be notified will ordinarily be, but need not be, the customer.

For each person who is to receive a death notice the system establishes one or more modes of transmission for the death notice and the address or addresses appropriate to each mode of transmission. At decision block 214 the system determines whether the notice of death is to be transmitted to its designated recipient by telephone. If not, the system moves to decision block 220 for facsimile notification. If the death notice is to be transmitted by telephone, a telephone number is obtained at block 216 and stored as shown at block 218. The system then determines at decision block 220 whether the death notice is to be transmitted by facsimile. If not, the system moves to block 226 for email. If the death notice is to be transmitted by facsimile, a facsimile number is obtained at block 222 and stored as shown at block 224. The system then determines at decision block 226 whether the death notice is to be transmitted by email. If not, the system moves to block 232 for surface mail. If the death notice is to be transmitted by email, an email address is obtained at block 228 and stored as shown at block 230. The system then determines at decision block 232 whether the death notice is to be transmitted by surface mail. If not, the system moves to block 238 for additional third party transmission. If the death notice is to be transmitted by surface mail, a surface mail address is obtained at block 234 and stored as shown at block 236.

At decision block 238 the system determines whether the death notice is to be transmitted to an additional third party. If so, the system moves back to block 112 where it obtains the name of this party and repeats the process just carded out for the customer. This process may be repeated for as many third parties as the customer desires. When no additional third party is to be notified the system moves to block 240 for accounting functions such as establishing the financial status of the account and depositing funds generated by the application.

2. Obtaining and Processing the Report of Death—FIG. 3.

Figure 3:
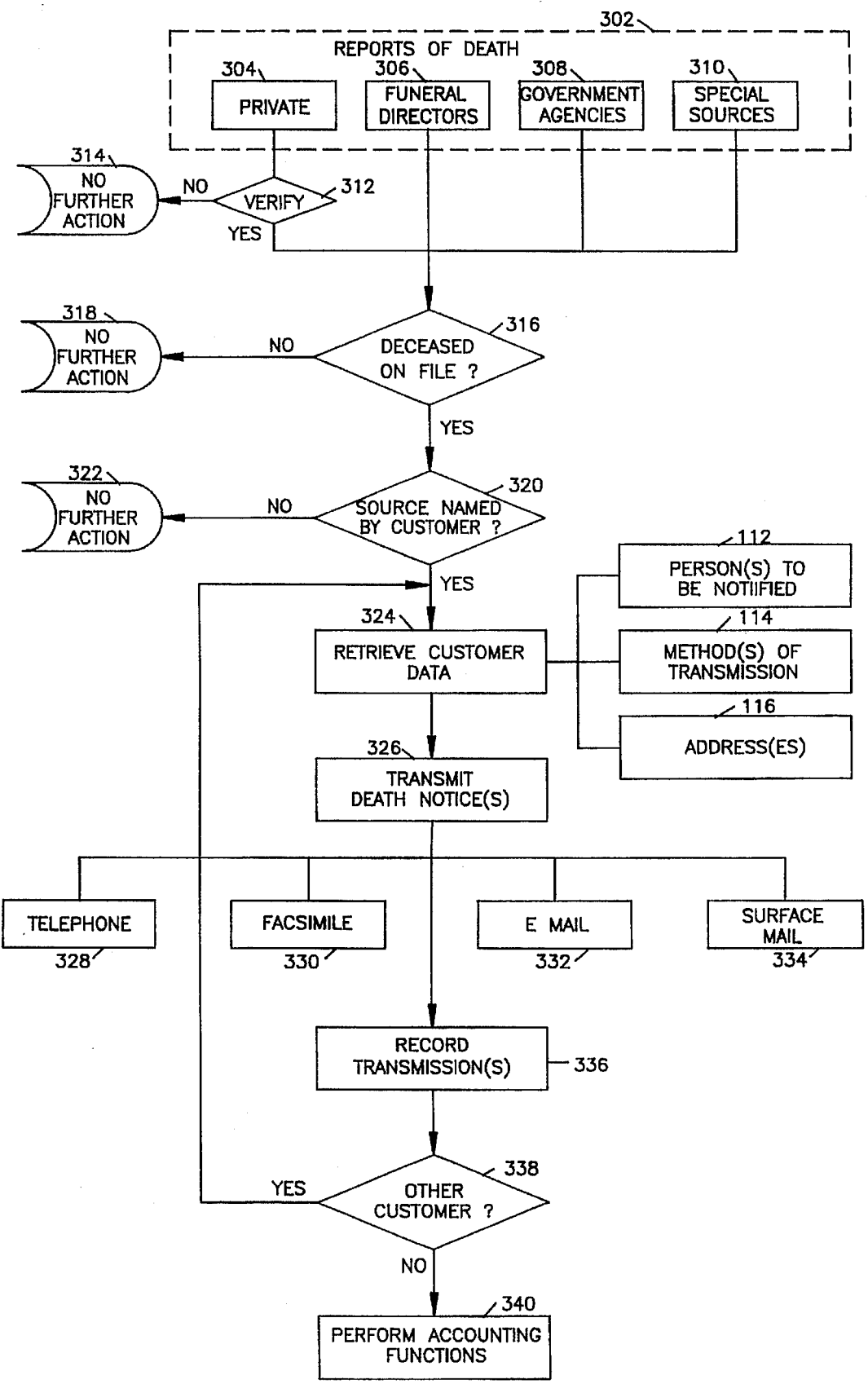
FIG. 3 is a flow diagram of the process of obtaining reports of death and transmitting the death notice.

The system provides for rapid processing of reports of death and communication of death notices, or obituaries. This operation, shown in FIG. 3, is initiated by reports of death 302 arising in the domain monitored by the depository. These reports of death may derive from government agencies 308, licensed funeral directors 306, special sources 310 or private sources 304 or from a combination of these.

The depository may select one or more government agencies 308 as one of the sources that it monitors for customers. In the United States state laws require that for every death a death certificate shall be filed in the clerk's office of the city or town in which the death occurred. If the deceased was a resident of another city or town an attested copy of this certificate is also sent to the clerk's office of that other city or town. From the city or town clerk's office the information contained in the death certificate is sent to the state department of health and vital statistics and from the latter office the information is forwarded to the federal level in both paper and electronic form. If the depository obtains reports from government sources these sources, in the interest of speed, would ordinarily be the city or town clerk's office. These reports are a matter of public record and, if monitored by the depository, would ordinarily be obtained daily and entered into the system manually or by modem where available in digital form.

Reports of death may also derive from special sources 310. Special sources here designate any sources other than government, funeral homes and private that the depository and its customer agree upon as a domain to be monitored. A leading example of special sources would be all the conventional death notices published in a certain newspaper or certain group of newspapers. It is assumed that in implementing this invention all necessary legal rights pertaining to matters of copywrite shall be duly secured by the depository. It may be noted, however, that while newspapers hold copywrite fights to most of the material they publish, including obituary columns written by their employees, they do not similarly hold copywrite rights to conventionally published death notices, or obituaries. The latter are paid announcements which, like advertisements, are commonly provided to competing newspapers.

In the preferred embodiment a special source that consisted of all the conventionally published death notices in a certain newspaper or certain group of newspapers, would be monitored by downloading daily from each monitored newspaper all the death notices published in each edition of that newspaper. The communication links necessary to effect this transfer of data are easily constructed by those skilled in the art. The depository extracts from the downloaded file the conventional notices of death together with any associated information and inputs this to the depository computer where it initiates the search process to be described later.

If the entity that owns the depository operates one or more newspapers, the depository has easy access to the information contained in the conventional death notices published in those newspapers. When the information for a death notice is received and keyed in for publication at the newspaper, it is transmitted also to the depository computer where it initiates the search process to be described later. This transmission may be effected either immediately or after the full day's batch of death notices has been received by the newspaper. In each case the depository will ordinarily obtain and process the reports of death and transmit appropriate obituaries to customers even before the newspaper whose conventional death notices are being monitored appears on the street.

Newspapers sometimes sell rights to the electronic distribution of material published in the newspaper after a brief time lapse, typically twenty four hours. If the entity that owns the depository also holds such fight of delayed electronic distribution, the depository may utilize the communication link already established. The depository would then extract from the digitized information of the downloaded newspaper file the data identifying the deceased in that newspaper's conventional death notices and input this, along with any associated information, to the depository computer where it initiates the search process to be described later.

If the depository does not purchase or otherwise arrange to receive data in digital form directly from the monitored newspaper the monitoring process may be carried out in the following way. The depository or its agent physically acquires the monitored newspaper when it first becomes available and either manually keys in or, with the aid of an optical scanner, scans in to the depository computer the information contained in that newspaper's death notices. This process of obtaining the information contained in the death notices may also be performed by a remote computer at sites distant from the depository and the resulting file transmitted to the depository where it initiates the search process to be described later.

It is expressly understood that the above description is not meant to limit the scope of the invention which can be embodied in other ways. The host computer of the depository may, for example, distribute its database to distant sites that are near the monitored newspapers. The newspaper data identifying the reported deceased may then be compared at those sites with the dam identifying persons whose deaths are to be reported to customers of the depository. The system may provide for the distant sites to process the reports of death to completion or it may provide for those sites to transmit only the matches to the depository host computer where the processing is completed.

Reports of death may also derive from licensed funeral directors 306. A major advantage in monitoring these sources is an increase in speed, because licensed funeral directors are ordinarily the ones who physically file the death certificate at the local clerk's office. Reports of death received from these sources will be processed typically a day before any conventional newspaper notice can publicize the death. The depository may even receive and process reports from these sources before the death certificate is filed at the local clerk's office.

Another advantage in monitoring funeral homes is increased assurance that certain deaths will be discovered. There is no legal requirement and hence no guarantee that any given death shall be publicized by a conventional newspaper death notice, let alone by one published in a particular newspaper. However, there is a legal requirement that every burial and cremation be performed by a duly licensed mortician or funeral director. The licensed morticians and funeral directors in any region are easily identified and the depository may attain any desired level of thoroughness in monitoring them. It will typically monitor for customers all deaths reported by a specified group of funeral homes agreed upon by the customer. Customers will select a group of funeral homes that is judged to include one that will handle the funeral of the awaited deceased. Different groups of funeral homes may be monitored for different customers or the same group of funeral homes may be monitored for all customers. Reports from funeral directors 306 would typically be obtained from funeral homes by telephone or facsimile for manual entry or by modem where available in digital form.

Reports of death may include also reports received from private sources 304 who are not licensed funeral directors. These sources are typically surviving family members who take responsibility for publicizing a death. These sources would become significant where the entity operating the depository also operates one or more funeral homes. They would become significant also where the depository has so established itself in a region as a leading disseminator of obituaries that the bereaved judge that those whom they wish to inform of the death are more apt to be customers of the depository with respect to the deceased than they are to be faithful readers of conventional obituaries published in a local newspaper.

When reports of death are received from private sources who are not licensed funeral directors they are verified for accuracy at block 312. This verification is ordinarily effected by asking the source to identify the funeral home that is handling the funeral and then contacting that funeral home for confirmation of the report. Funeral directors now readily make available the names of the newly deceased whose funerals they are handling to newspapers seeking verification in the conventional system. Verification may also be effected by comparing the name and address of the reported deceased with a continually updated list of the names and addresses of those whose funerals are being handled by the funeral home cited in the private report as reference. If there is no verification, further action on the report terminates as shown at block 314. If there is verification the report proceeds with other reports of death to decision block 316.

At decision block 316 the depository determines whether the deceased is on file as a person of whose death a customer has contracted to be informed when report of the death is received. It searches its database of persons who are the awaited deceased and compares the data identifying the newly reported deceased with a corresponding data set identifying each of the awaited deceased. The address of the deceased is typically auxiliary data used to prevent matches with possible deceased persons of the same name who do not concern the customer. If there is no match, further action on the report terminates as shown at block 318.

If there is a match the system determines at block 320 whether the customer contracted to be notified of the death if reported by the source from which it now emanates. If not, further action terminates as shown at block 322. This step of the process is optional and is omitted where the depository monitors the same source or same set of sources for all customers.

If the customer is to be notified of the death reported, the system moves to block 324 where it retrieves the stored customer data specifying the person or persons to be notified 112, the method or methods of transmission 114 and the address or addresses appropriate to each method of transmission 116. It then begins output at block 326. Telephoned notification 328 may be manual or automated with a voice recording. Facsimile 330 and email 332 transmissions may be effected directly from the computer via the communications modem. Surface mail transmission occurs as shown at block 334.

The system then proceeds to block 336 where it records the transmission or transmissions to the customer file to block a further transmission of the same death notice by the same means to the same person. This step is taken to prevent redundant transmissions where reports of the same death are received from different sources. The record is also used in removing information needed for the matching process from the system when all transmissions have been completed, since the death is an unrepeatable event. The system then moves to decision block 338 and determines whether any other customer has contracted for notification of the death reported. If there is another customer the system moves back to block 324 and repeats the process carried out for the preceding party. If there is no further person to receive notice of the death, the system moves to block 340 and performs such accounting functions as billing the customer.

The set of sources, or domain, that the depository takes responsibility for monitoring may be expanded or contracted to any degree. It may be geographically restricted or indefinitely extended. It may also be defined by various parameters. The depository may monitor only one source, or only one set of sources, for all customers or it may offer customers choices as to the sources monitored. It may offer a variety of options with respect to the way in which the obituary is transmitted or it may offer few or no such options.

3. Use of the System for Those Publicizing a Death

The method and system of the present invention may be used also to serve those concerned not with discovering but publicizing a death or memorial service. Such persons are able to submit obituary information directly to the depository and to designate certain third parties to receive it. With the depository acting in his or her stead, the bereaved family member need not even appear as the author of the communication. Those who will not attend the service have an opportunity to compose a written response or even to decide on reflection that it would be better to be present. Any sense of confrontation or test of friendship is attenuated and family members can without awkwardness individually notify marginal friends as well as acquaintances whose relationship with the deceased is uncertain, thereby solving the problem of direct personal notification explained in the description of the background of the invention. When combined with supplemental newspaper publication, the method will sometimes result in a selection of newspapers different from that made when the conventional system is the only one available.

Figure 4:
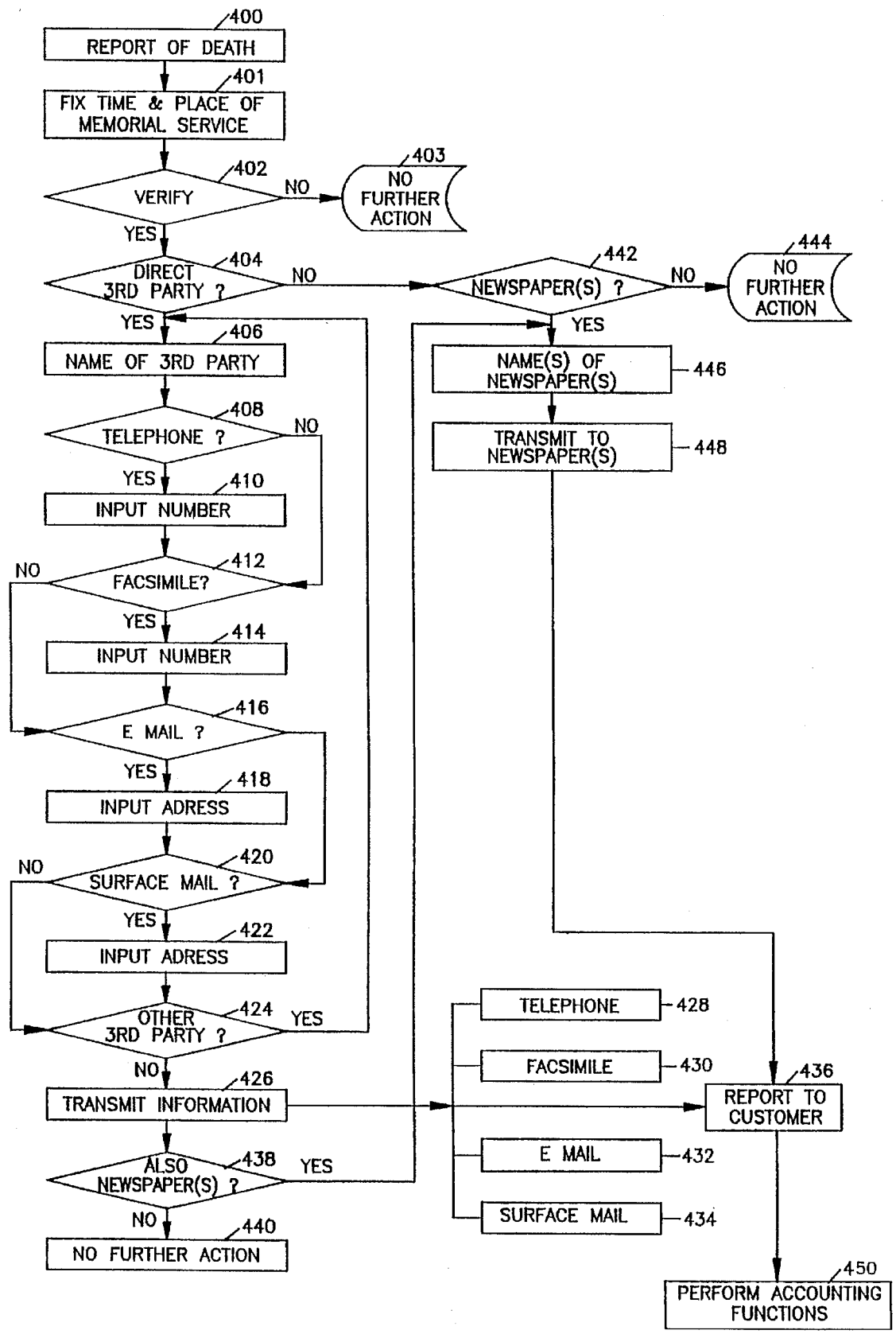
FIG. 4 is a flow diagram of the method of the present invention as used for customers concerned with disseminating notice of a death that has already occurred.

A block diagram of the system used in this way is presented in FIG. 4. The process differs from that shown in FIG. 2 and FIG. 3 essentially in being performed by an entity which, serving those concerned with disseminating notice of a death that has already occurred, need not engage in the same extensive monitoring activity.

The report of death and any associated information is received from the customer as shown at block 400. The time and place of memorial services are fixed as shown at block 401, usually by obtaining this information from the customer who is the source of the report. The information is verified for accuracy at block 402. This verification is ordinarily effected by asking the customer who is reporting the death to identify the funeral home that is handling the funeral and then contacting that funeral home for confirmation. This step relating to verification is optional and is omitted where the entity using the method already has evidence that the information is correct. This would be the case, for example, where the entity using the method was itself the funeral home that was handling the funeral. If there is no verification further action terminates as shown at block 403.

If there is verification the system moves to decision block 404 where it determines whether the customer wishes any third party to receive individual but depository mediated notification of the death and memorial services. If not, the system moves to block 442 for newspaper dissemination. If no newspaper is to publish the death notice further action terminates as shown at box 444. The latter two steps relating to newspaper dissemination are included because in opening a new route for the communication of the death notice and creating the option for individual but depository mediated third party notification a new factor is introduced to the decision as to which newspaper or which combination of newspapers shall be selected for publication of a conventional death notice. It is, therefore, a decision different from the decision made when the conventional system of disseminating death notices is all that is available, even when the same combination of newspapers turns out to be the one selected. If the customer does want a third party to receive depository mediated individual notification of the death or memorial service the system moves to block 406 and obtains the name of that third party.

The system then determines at decision block 408 whether the notice of death and memorial service is to be transmitted to that third party by telephone. If not, the system moves to decision block 412 for facsimile notification. If the information is to be transmitted by telephone, a telephone number is obtained as indicated at block 410. The system then moves to decision block 412 and determines whether the notice of death and memorial service is to be transmitted by facsimile. If not, the system moves to block 416 for email transmission. If the information is to be transmitted by facsimile, a facsimile number is obtained as shown at block 414. The system then moves to decision block 416 and determines whether the information is to be transmitted by email. If not, the system moves to block 420 for surface mail. If the death notice is to be transmitted by email, an email address is obtained as shown at block 418. The system then moves to decision block 420 and determines whether the information is to be transmitted by surface mail. If not, the system moves to block 424 for other third party transmission. If the information is to be transmitted by surface mall, a surface mall address is obtained as shown at block 422.

The system then moves to decision block 424 where it determines whether the notice of death and memorial services is to be transmitted to any other third party. If so, the system moves back to block 406 where it obtains the name of that third party and repeats the process carded out for the preceding third party. If there is no further third party to receive notification the system transmits the notice of death and memorial services to the designated third party or parties as indicated at block 426. The information is transmitted by telephone 428, facsimile, 430, email 432, surface mail 434 or the combination of these as specified by the customer. Since the entity using the method acts in the customer's stead the customer need not even appear as the author of the communication. A report for the customer is prepared as shown at block 436 and accounting functions are performed as indicated at block 450.

The system then moves to decision block 438 and determines whether the death notice is also to receive supplemental conventional publication in one or more newspapers. If not, further action terminates as indicated at block 440. If a conventional death notice is to be published in one or more newspapers the names of these newspapers are obtained as shown at block 446 and the information, including any associated obituary information obtained with the report of death, is transmitted as shown at block 448. The latter three steps relating to newspapers are included because in opening a new route for communication of the death notice and creating the option for depository mediated individual third party notification a new factor is introduced to the decision as to which newspaper or which combination of newspapers will be selected for conventional publication of the obituary. It is, therefore, a decision different from the decision made when the conventional system of disseminating obituaries is all that is available, even when the same combination of newspapers turns out to be selected. The system then moves to block 436 where it reports the newspaper transmissions and at block 450 performs the associated accounting functions.

The method of the present invention may be used also for persons anticipating their own death or that of a family member. In this case the customer typically assumes responsibility for arranging that the depository receive a report of the death when it occurs. The customer may, for example, in the course of making preplanned funeral arrangements provide for this communication to be made by the funeral home to the depository. This communication will not be necessary if the funeral home is itself acting as the depository or as its agent.

Figure 5:
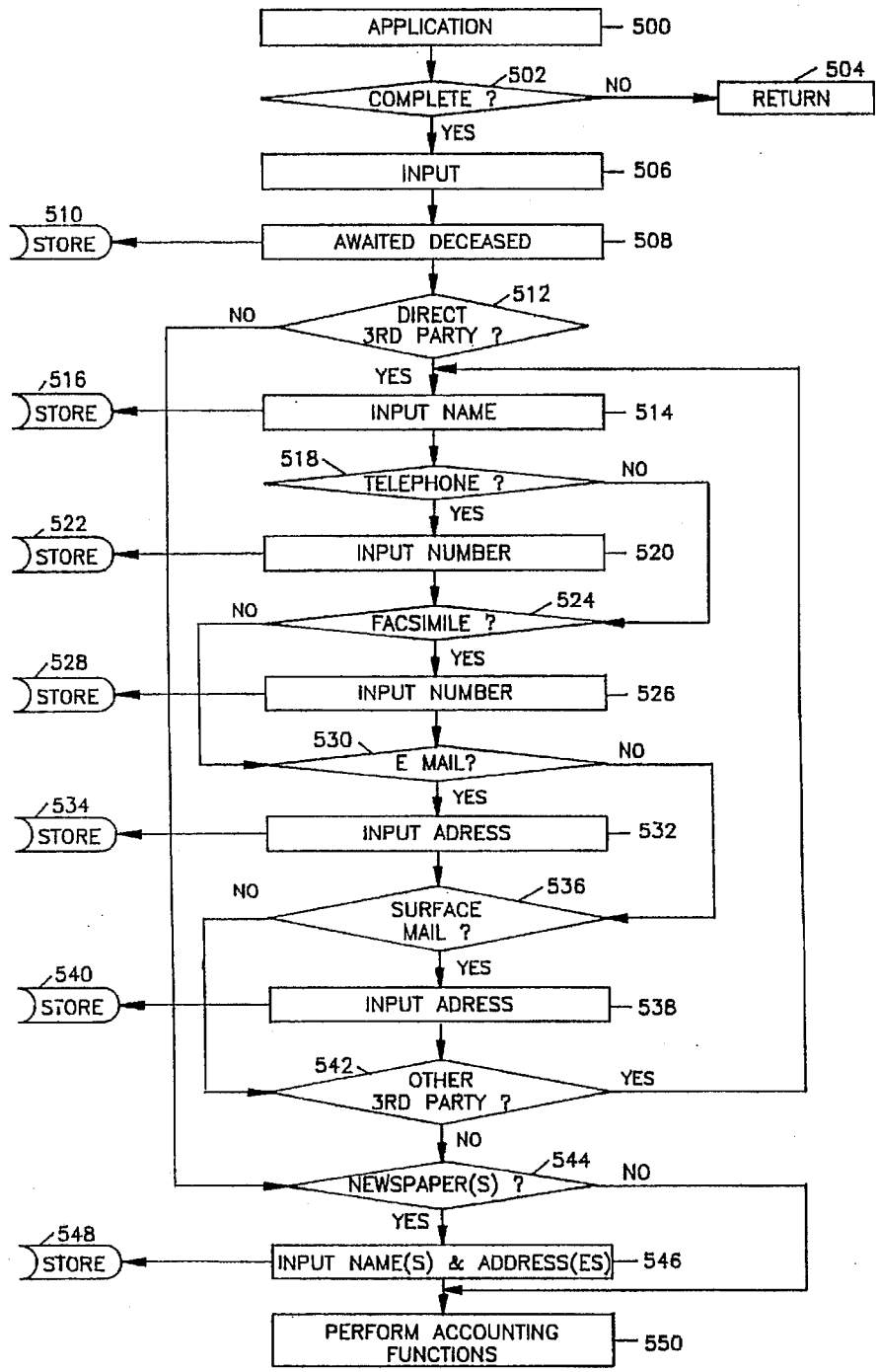
FIG. 5 is a flow diagram of the customer application process of the present invention as used for customers concerned with disseminating notice of their own future death.

FIG. 5 is a flow diagram of the customer application process for use of the method in this way. This process, and its companion process shown in FIG. 6, differ from those shown in FIG. 2 and FIG. 3 essentially in being performed by an entity which, because it serves primarily those concerned with disseminating a notice of death that has already occurred, need not engage in the same extensive monitoring activity.

Turning now to FIG. 5, the application is received at block 500 and at decision block 502 is checked for completeness and for omissions that would make it impossible to provide a service requested. If the information is incomplete or contains obvious errors the application is returned to the customer at block 504 with a request for additional information. When the application is complete the input of information and instructions occurs as indicated at block 506. The name of the awaited deceased, who is ordinarily the customer, with any associated information is entered at block 508 and stored as shown at block 510. Associated information may include special biographical information destined for supplementary conventional newspaper publication. The system then moves to decision block 512 and determines whether there is to be any depository mediated individual third party notification of the death or memorial service. If not, the system moves to block 544 for newspaper publication. If them is to be individual third party notification, the system moves to block 514 where the name of that third party and any associated information is obtained and stored as shown at block 516. This associated information may include special information intended only for that party.

The system then moves to decision block 518 and determines whether the notice of death or memorial services is to be transmitted to that third party by telephone. If not, the system moves to decision block 524 for facsimile notification. If the death notice is to be transmitted by telephone, a telephone number is obtained at block 520 and stored as shown at block 522. The system then moves to decision block 524 and determines whether the notice of death is to be transmitted by facsimile. If not, the system moves to block 530 for email transmission. If the death notice is to be transmitted by facsimile, a facsimile number is obtained at block 526 and stored as shown at block 528. The system then moves to decision block 530 and determines whether the death notice is to be transmitted by email. If not, the system moves to block 536 for surface mail. If the death notice is to be transmitted by email, an email address is obtained at block 532 and stored as shown at block 534. The system then moves to decision block 536 and determines whether the death notice is to be transmitted by surface mail. If not, the system moves to block 542 for any other third party transmission. If the death notice is to be transmitted by surface mail, a surface mail address is obtained at block 538 and stored as shown at block 540.

The system then moves to decision block 542 and determines whether the notice of death and memorial service is to be transmitted to another third party. If so, the system moves back to block 514 where it obtains the name of that third party and repeats the process carried out for the preceding third party. If no other third party is to receive a notice of death the system moves to decision block 544 where it determines whether the death notice is also to receive conventional newspaper publication. This step is included because in opening a new route for communication of the death notice and creating the option of depository mediated individual third party notification a new factor is introduced to the decision as to which newspaper or which combination of newspapers shall be selected for publication of a conventional death notice. It is, therefore, a decision different from the decision made when the conventional system of disseminating death notices is all that is available, even when the same combination of newspapers turns out to be selected. If the death notice is not to receive also conventional newspaper publication the system moves to block 550 for accounting functions. If the death notice is also to be published in one or more newspapers the system moves to block 546 where the name and address of the newspaper or newspapers is obtained and stored as shown at block 548. The information destined for newspapers may include biographical information not included in transmissions to third parties. The system then moves to block 550 for accounting functions such as billing the customer. The information obtained from the application remains stored until the report of death is received and the time and place of memorial services established, at which time the information is transmitted to the various parties in the manner and at the addresses specified.

Figure 6:
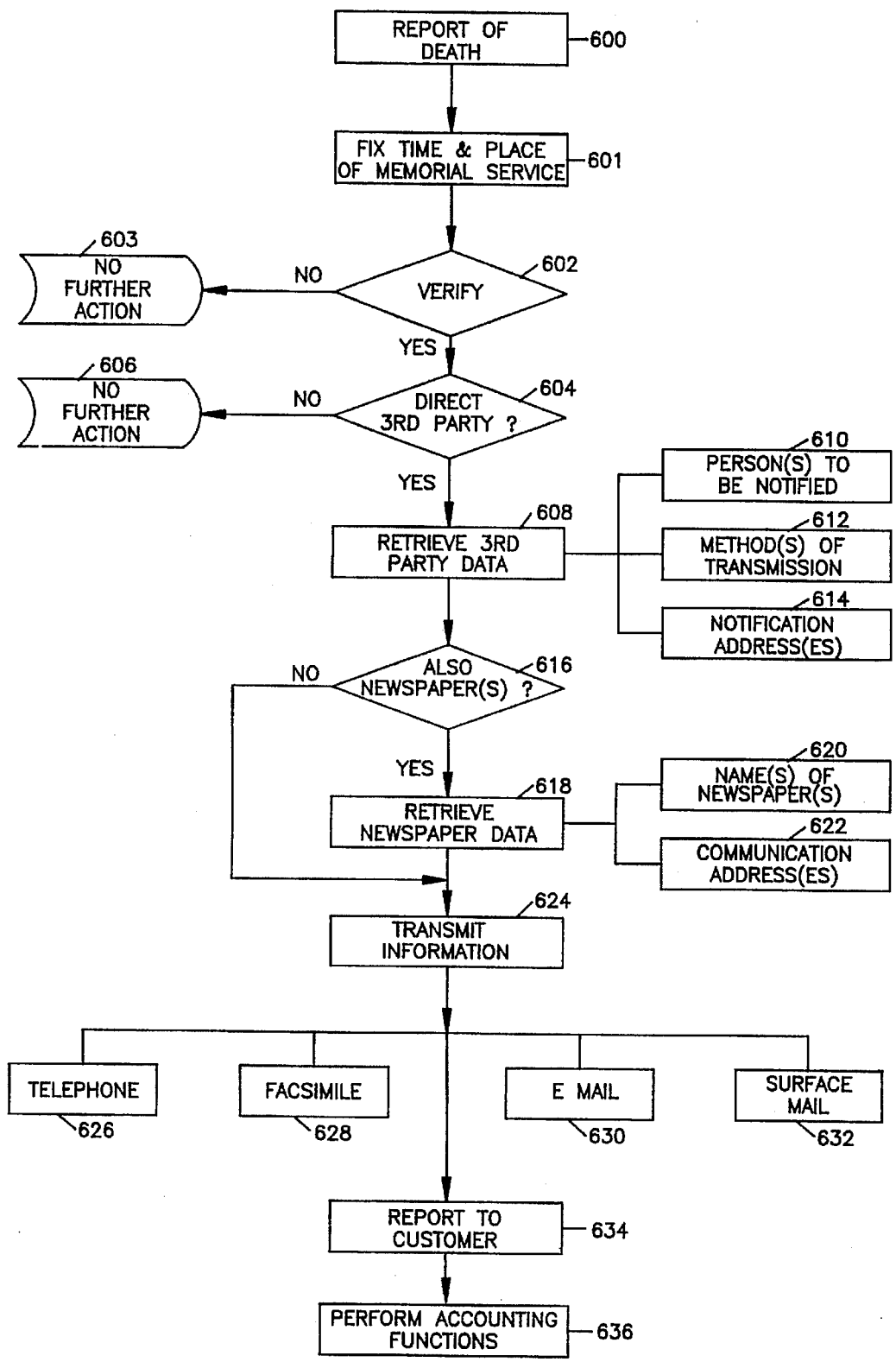
FIG. 6 is a flow diagram of the process of disseminating notice of death by the method of the present invention as used for customers who planned for the dissemination of the notice of their own death.

When the report of death is actually received the process of disseminating the notice of death is carried out as shown in FIG. 6. The entity using the method and system of the present invention receives the report of death together with any auxiliary information, as shown at block 600. The time and place of memorial services are fixed as shown at block 601, ordinarily by obtaining this information from the source of the report. The information is verified for accuracy as shown at block 602. This verification is effected by asking the source of the report to identify the funeral home that is handling the funeral and then contacting that funeral home for confirmation. If there is no verification further action terminates as shown at box 603. The latter two steps relating to verification are optional and are omitted where the entity using the method already has evidence that the information is correct. This would be the case, for example, where the entity using the method was itself the funeral home that was handling the funeral.

If there is verification the system moves to decision block 604 and determines whether provision has been made for third party notification. This is a record check to confirm the presence of the information necessary to provide the expected service. The system searches its record of stored information for the pertinent dam obtained through the application process shown in FIG. 5. If it finds that no provision for third party notification was made, action terminates as shown at block 606. The reporting source may then be invited to obtain the desired service through the process described in the explanation of FIG. 4.

Returning to FIG. 6, if provision has been made for third party notification, the system moves to block 608 and retrieves the data relating to transmission to the designated third parties. This data includes the name of the person or persons to be notified 610, the method or methods of transmission 612 and the addresses appropriate to the methods of transmission 614. The system then determines at block 616 if the obituary is also to receive conventional newspaper publication. If not, the system moves to block 624 for transmission of the information. If one or more newspapers is to publish this information, the system retrieves at block 618 the data relating to newspaper notification, which includes any special information destined only for the newspapers. If necessary, this information may be updated by a family member before incorporation into the notice of death and memorial services. The retrieved data includes the name of the newspaper or newspapers, 620, and the appropriate newspaper address or addresses 622. The system then moves to block 624 where it transmits the information to the newspapers and to the designated third parties at the addresses specified by telephone 626, facsimile, 628, email 630, surface mail 632 or by the combination specified by the customer. A report is issued for the customer as shown at block 634 and at block 636 the system performs such accounting functions as billing the customer.

It is expressly understood that the above described embodiment is for explanatory purposes and is not meant to limit the scope of the invention. The system encompasses other embodiments and modifications as well, including those in which some of the steps described are performed without a computer and those in which the information is processed in a different number of sequential steps. This invention addresses the deficiency of the conventional system as it affects both those concerned with discovering and those concerned with publicizing a certain death. The entity using it may serve both of these groups or it may confine its services to only one of them. The scope of the invention is to be determined by the appended claims and their legal equivalents rather than by the examples given.

I claim:

1. A system for administering a depository for disseminating obituaries, said system comprising:

(a) means for creating a first database of customers each of whom has selected at least one person as a person of whose death one or more parties identified by said customer shall be notified if a report of said death arises in a domain predetermined in an agreement with said customer;

(b) means for creating a second database of persons each of whom has been selected by at least one customer as a person of whose death one or more parties identified by said customer shall be notified if a report of said death arises in said predetermined domain;

(c) means for receiving reports of death arising in said predetermined domain;

(d) means for comparing data identifying each person whose death is reported in said predetermined domain with data identifying each of said persons selected by at least one customer as a person of whose death one or more parties identified by said customer shall be notified if a report of said death arises in said predetermined domain;

(e) means for transmitting a notice of death, where there is a match, to said parties identified by said customers as parties to be notified of that particular death.

2. The system of claim 1 wherein said one or more parties to be notified of said death includes said customer.

3. The system of claim 1 wherein said predetermined domain includes at least one funeral home.

4. The system of claim 1 which further includes means for transmitting said notice of death in a way selected by said customer.

5. A method for disseminating obituaries comprising the steps of:

(a) creating a first database of customers each of whom has selected at least one person as a person of whose death at least one party identified by said customer shall be notified if a report of said death arises in a domain predetermined in an agreement with said customer;

(b) creating a second database of persons each of whom has been selected by one or more customers as a person of whose death said one or more parties identified by said one or more customers shall be notified if a report of said death arises in said predetermined domain;

(c) receiving reports of death arising in said predetermined domain;

(d) comparing data identifying each person whose death is reported in said predetermined domain with data identifying each of the persons selected by said one or more customers as a person of whose death said one or more parties identified by said one or more customers shall be notified if a report of said death arises in said predetermined domain;

(e) transmitting a notice of death, where there is a match, to said one or more parties identified by said one or more customers as parties to be notified of that particular death.

6. The method of claim 5 wherein said one or more parties to be notified of said death includes said customer.

7. The method of claim 5 wherein said predetermined domain includes at least one funeral home.

8. The method of claim 5 wherein said notice of death is transmitted in a way selected by said customer.

* * * * *